(12) United States Patent
Richards et al.

(10) Patent No.: US 7,994,453 B2
(45) Date of Patent: Aug. 9, 2011

(54) FLASH HEATING FOR TUBING

(75) Inventors: Keith A. Richards, Manchester, NH (US); Stephen N. Bunker, Wakefeield, MA (US)

(73) Assignee: Implant Sciences Corporation, Wilmington, MA (US)

( * ) Notice: Subject to any disclaimer, the term of this patent is extended or adjusted under 35 U.S.C. 154(b) by 592 days.

(21) Appl. No.: 12/077,190

(22) Filed: Mar. 17, 2008

(65) Prior Publication Data
US 2009/0230111 A1  Sep. 17, 2009

(51) Int. Cl.
*H05B 1/00* (2006.01)
*B01D 59/44* (2006.01)

(52) U.S. Cl. ........ 219/201; 392/387; 250/281; 250/287; 250/288; 250/290

(58) Field of Classification Search .................. 219/201; 392/387; 250/281, 287–8, 290
See application file for complete search history.

(56) References Cited

U.S. PATENT DOCUMENTS

| | | | |
|---|---|---|---|
| 5,310,681 A * | 5/1994 | Rounbehler et al. | 436/106 |
| 6,828,795 B2 | 12/2004 | Krasnobaev et al. | |
| 6,861,646 B2 | 3/2005 | Motchkine et al. | |
| 6,888,128 B2 | 5/2005 | Krasnobaev et al. | |
| 2003/0155504 A1 | 8/2003 | Motchkine et al. | |
| 2004/0227073 A1 | 11/2004 | Kranobaev et al. | |
| 2004/0248319 A1 | 12/2004 | Belyakov et al. | |
| 2005/0007119 A1 | 1/2005 | Belyakov et al. | |
| 2006/0214580 A1 | 9/2006 | Bunker et al. | |
| 2007/0180933 A1 | 8/2007 | Grate et al. | |

* cited by examiner

*Primary Examiner* — Shawntina Fuqua
(74) *Attorney, Agent, or Firm* — Muirhead and Saturnelli, LLC

(57) ABSTRACT

A chemical sample gas tube that is capable of being rapidly heated and cooled allows rapid purging of condensed chemical vapor from its inside surface. The tube may include a thin foil with an electrically conducting surface, a rigidly separated pair of clamps to shape the thin foil into a cylinder shape, and a temperature-controlled source of electricity that can flow sequentially through the clamps and thin foil for heating. The temperature of the cylindrical thin foil may be increased at a rate of at least 25 degrees Celsius per second, and may be cooled at a rate of at least 10 degrees Celsius per second. A temperature control sequence may be provided that includes at least one temperature that performs at least one of: condensing the chemical vapor, transmitting the chemical vapor, desorbing the condensed chemical vapor, and decomposing the condensed chemical vapor.

16 Claims, 11 Drawing Sheets

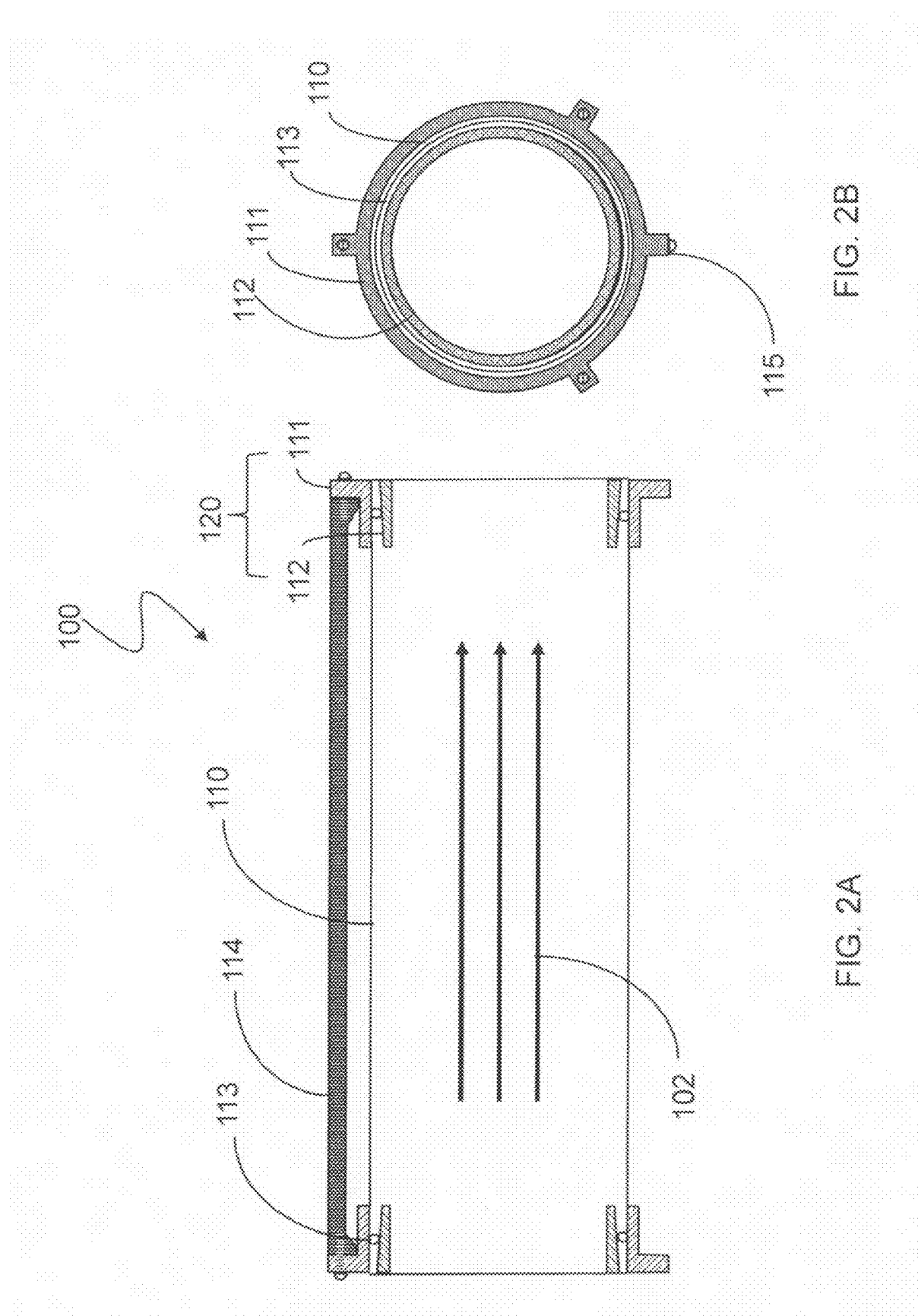

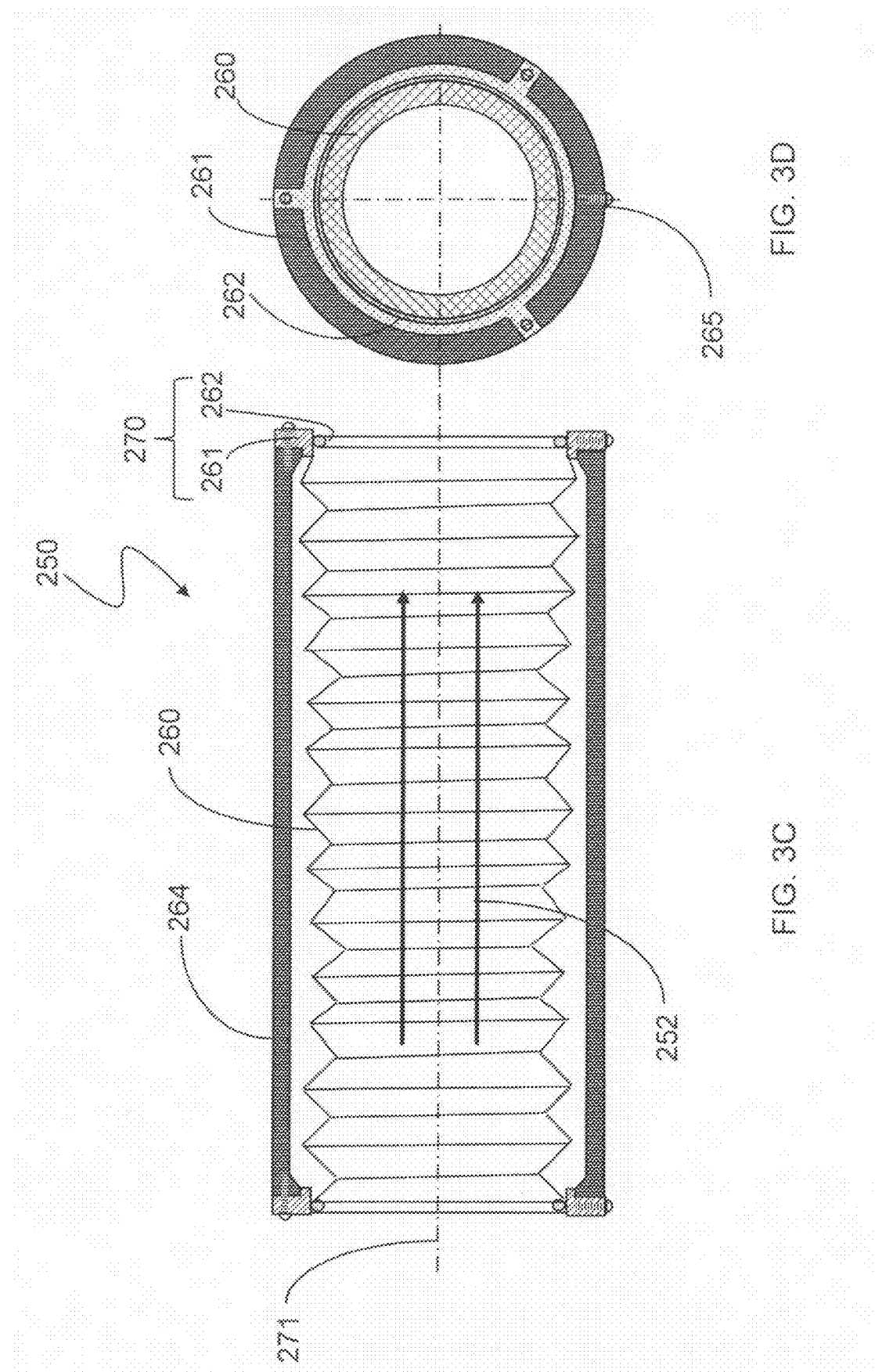

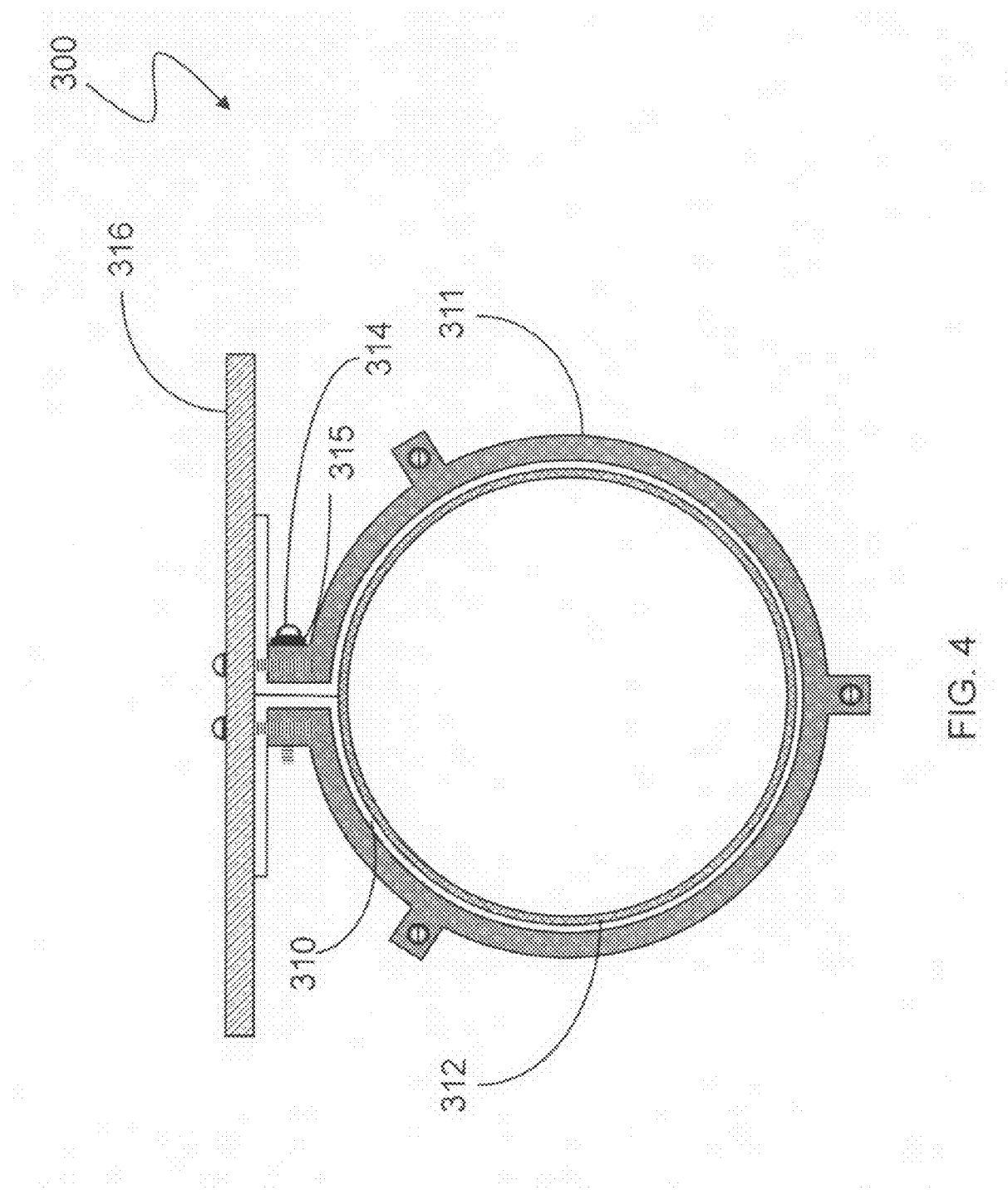

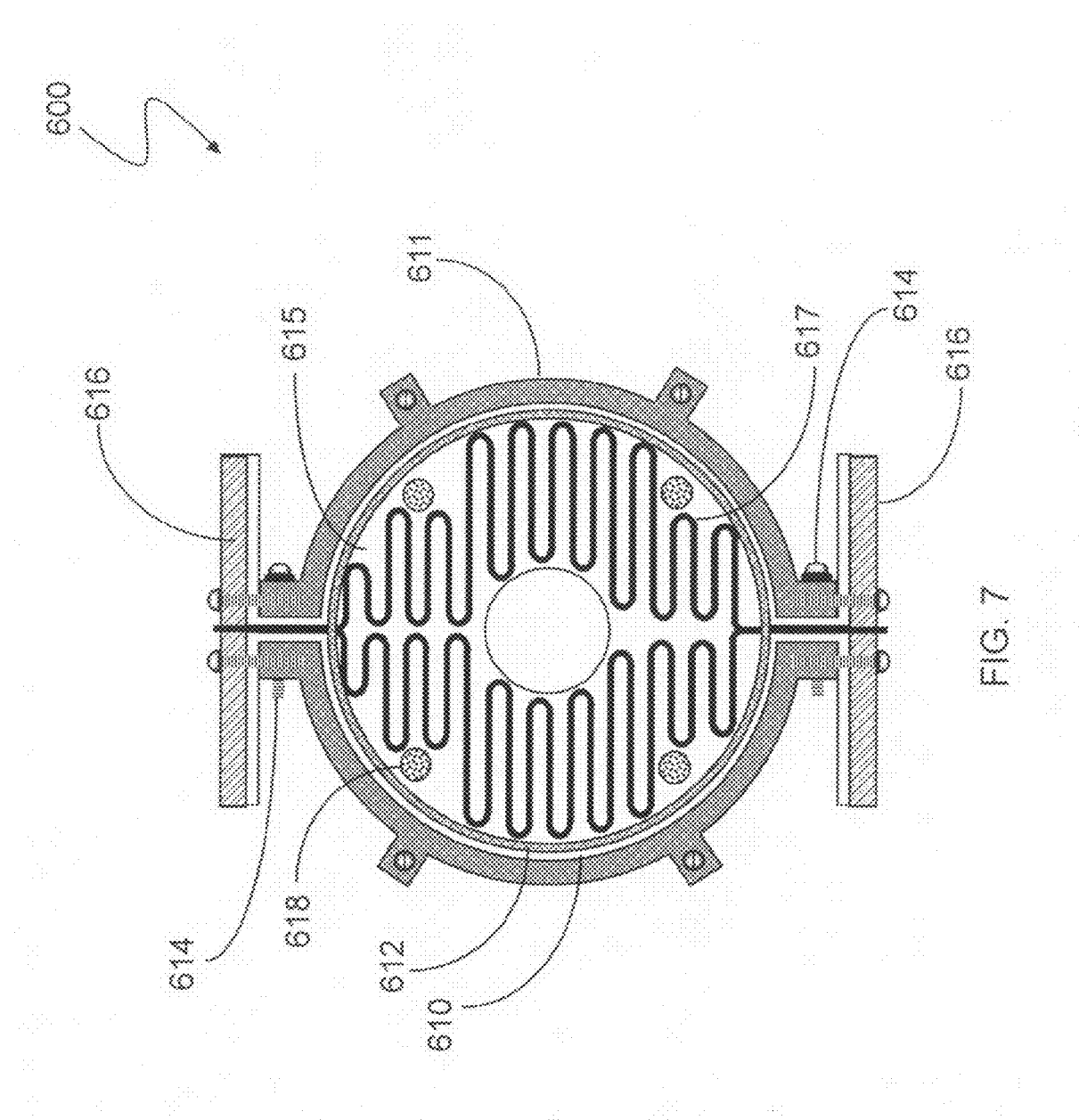

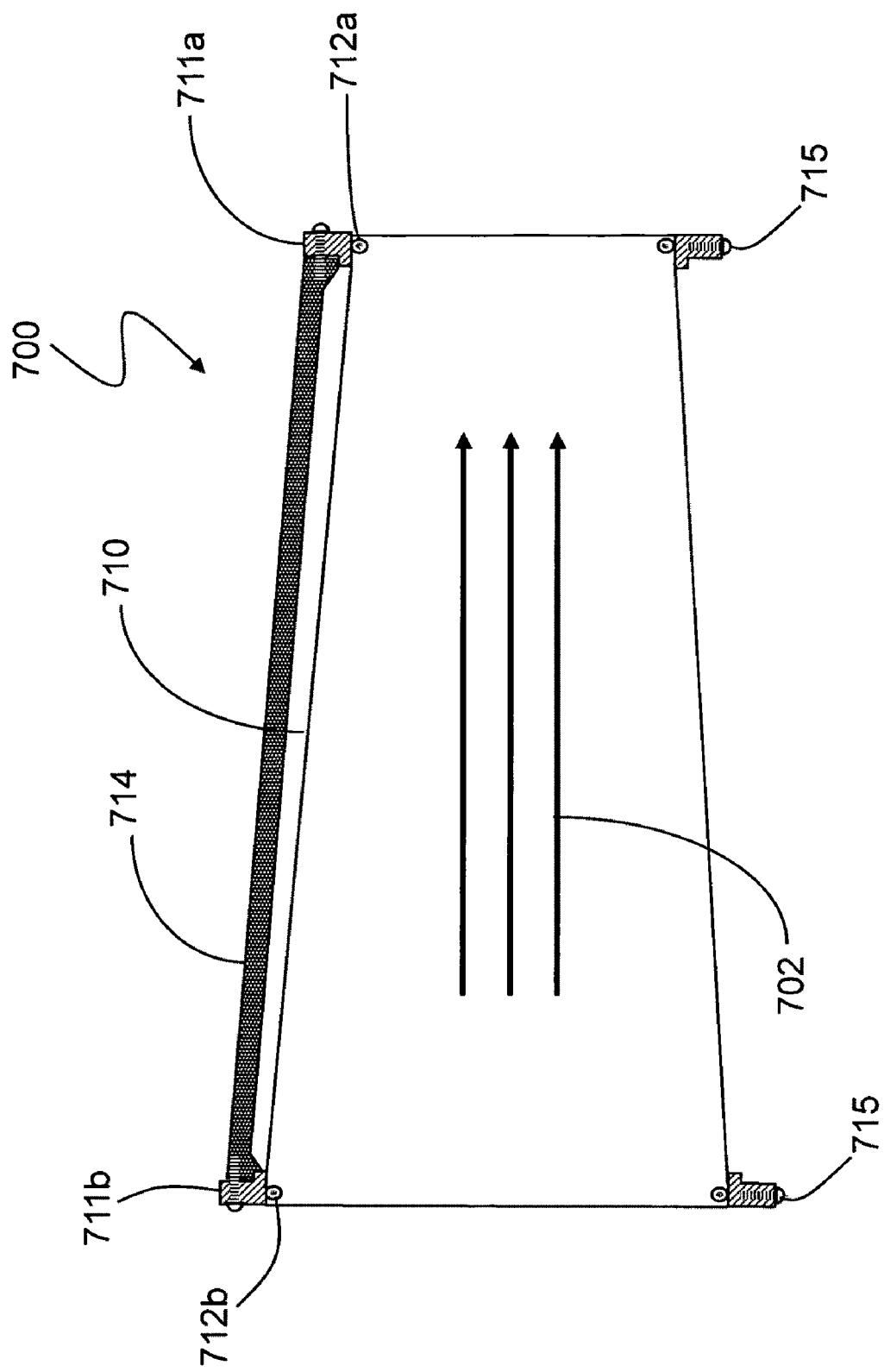

FLASH HEATING FOR TUBING

BACKGROUND OF THE INVENTION

1. Field of the Invention

This application relates to the field of detection of chemical substances and, more particularly, to improving the transport of vapors of chemical substances through tubing.

2. Description of Related Art

Chemical detection may be performed by a variety of detection instruments, such as a gas chromatograph, an ion mobility spectrometer, a mass spectrometer, and/or a differential mobility spectrometer. Many of these chemical detectors require that a chemical sample be vaporized and transported through a length of tubing (the "sample tube") to reach the detection component. In order to avoid condensation of chemical species contained within the vapor sample (the "sample gas"), the walls of the sample tube may be heated.

In some cases, the process of taking a sample begins with an operator rubbing an absorbent substance (the "sample trap"), such as chemical filter paper, onto the surface to be tested. Particles of the chemical of interest may then be transferred and concentrated on the absorber. This sample trap is then brought to the vicinity of the sampling orifice of the chemical detector. The quantity of particles of the target substance on the target surface is usually very small, often corresponding to only nanograms or even picograms of particles per square centimeter. The chemical detector must be very sensitive to identify a valid signal from evaporated target molecules when the initial concentration and surface area of target particles is so small compared to possible background contamination.

A known technique for vaporizing the sample that is commonly employed is to provide a heated zone (the "desorber") that resembles an oven. The desorber may completely enclose the sample trap when operating or may have an open entrance to facilitate the insertion of a sample trap. A gas pump draws the sample gas from the desorber into the sample entrance orifice of the chemical detector through a sample tube. A second embodiment for chemical species that have a sufficiently high vapor pressure at room temperature is to only provide a sample tube in pneumatic communication with the external environment and the sample entrance orifice of the chemical detector together with a gas pump to draw sample gas into the chemical detector.

The chemicals that may be drawn through the sampling tube may have a wide variety of physical properties. In particular, the most significant properties for this discussion are the vapor pressure as a function of temperature, the rate of adsorption on the inside surface of the sampling tube as a function of temperature, and the decomposition rate at the temperature of the sampling tube.

The vapor pressure is important, because a low vapor pressure substance is more likely to partially condense on the inside surface of the sampling tube when a concentrated pulse of sample gas passes through the sampling tube. Subsequent slow re-evaporation of the temporarily condensed sample gas leads to equipment downtime until all previous chemical substance has been purged from the chemical detector system.

The substance that comprises the inside surface of the sampling tube may have greater or less affinity for adhesion ("adsorption") of a specific chemical in the sample gas. Adsorption is a function of the temperature as well as the substance of the inside surface of the sampling tube. In general, higher temperature leads to less adsorption.

Decomposition of the chemical can potentially create new chemicals and deposit low vapor pressure decomposition products on the inside surface of the sampling tube. Sufficient temperature can fully decompose most organic materials to substances with virtually no vapor pressure. Decomposition may also undesirably selectively remove a target gas species from the sample gas, and this limits the maximum temperature that is acceptable for the sample tube when sample gas is flowing through it.

Rapid purging of unwanted sample gas chemicals from the inside of the sampling tube is significant for minimizing the time required to return a chemical detector to its "ready" condition. If too hot a sampling tube is employed, decomposition into unwanted substances may occur and even decompose chemical species of interest. If too cold a sampling tube is employed, excessive condensation and lengthy purging time will be required. Normally, the temperature of the sampling tube may be a compromise between these two extremes, and ambient chemical species will eventually be encountered that lead to an undesirably long purging time and consequently a lengthy "down time" of the chemical detection instrument.

Accordingly, it would be desirable to provide a system that addresses the above-noted issues and improves the processes related to transporting vapors of chemical substances through tubing.

SUMMARY OF THE INVENTION

According to the system described herein, a method providing a gas sampling tube includes providing a foil with an electrically conducting surface. A first clamping mechanism clamps the foil into an annular shape at a first end of the annular shape. A second clamping mechanism clamps the foil into the annular shape at a second end of the cylinder. A source of electricity supplies a flow of electricity sequentially through the first clamping mechanism, the foil, and the second clamping mechanism in order to heat the foil. The first clamping mechanism and the second clamping mechanism are separated by at least one separator to provide structural rigidity to the cylinder. A controller is provided that controls the source of electricity and permits the temperature of the foil to be increased at a rate of at least 25 degrees Celsius per second, wherein a temperature sequence including at least one temperature of the foil is controlled according to performance of at least one of: condensing chemical vapor, transmitting chemical vapor, desorbing condensed chemical vapor, and decomposing condensed chemical vapor.

According further to the system described herein, the foil may be either a metal foil, a polymer coated with a conducting material, a flexible ceramic coated with a conducting material, and/or a laminate of metal and electrical insulator. The metal foil may be selected from: an alloy containing nickel, such as Inconel, a low thermal expansion alloy, such as Invar, and a stainless steel. The metal foil may be a composite of two or more metals. The polymer that is coated with a conducting material may have a melting or decomposition point greater 200 degrees Celsius. The polymer that is coated with a conducting material may be selected from a polyimide, such as Kapton, an aramid, such as Nomex, a fluorocarbon, such as Teflon, and/or a poly ether ketone, such as polyetheretherketone (PEEK). The flexible ceramic may be a form of mica.

According further to the system described herein, the clamp mechanism may embed the foil between two swaging rings, between a cylindrical ring and a snap ring, and/or between a cylindrical ring and a circular spring. The clamp mechanism may further optionally include at least one of a deformable electrically conductive metal o-ring, a deformable electrically conductive metal wire, and a deformable electrically conductive metal foil in contact with the electrically conducting surface of the foil in order to improve the transport of electricity between the clamp mechanism and the foil. Examples of deformable electrically conductive metal include gold, indium, silver, copper, nickel, tin, lead, and some alloys containing substantially these elements.

According further to the system described herein, the foil may initially be rectangular in shape such that the foil is wrapped into a straight cylinder of constant diameter or the foil may be trapezoidal shaped so that said foil is wrapped into a cone-shaped sample tube of variable diameter. The description of embodiments of the system described herein referencing cylinders or cylindrical shapes in reference to sample tubes of fixed cross sectional diameter may also be used in connection with embodiments for tubes having other annular shapes, including shapes having a variable cross sectional diameter, such as a cone. Orifices may be positioned at suitable locations in the foil to permit tee-connections to other tubes. Further, at least one of the first clamping mechanism and the second clamping mechanism may be twisted about a common central axis of the clamping mechanisms to wrinkle a surface of the foil clamped in the annular shape, wherein a twist of the foil is maintained by fixed connections to the separator.

According further to the system described herein, when the core of the foil is an electrical insulator, the electrically conducting coating or laminate may be uniformly distributed on at least one face of the foil, distributed in a pattern on at least one face of the foil, or in any combination thereof. A uniform distribution may be inexpensive to prepare and useful for heating the foil uniformly. A patterned distribution may be useful for special applications, such as creating a thermal gradient or forming a voltage gradient. A combination of a uniform distribution on one face and a patterned distribution on the other may be useful for combining uniform heating and the formation of a voltage gradient.

According further to the system described herein, the source of electricity may be connected between the first and second clamping mechanisms. The structural separator of the first and second clamp mechanisms may be electrically insulating and may be in the form of hollow tubing, rod spacers, and/or a connection to an external rigid frame. The separator of the first and second clamping mechanisms may further include thermal insulation.

According further to the system described herein, the first and second clamping mechanisms may be slightly twisted in opposite directions about their central axis in order to add wrinkles to the surface of the foil. Attachment of the first and second clamping mechanisms to the structural separator of the first and second clamping mechanisms may be used to maintain the twist and the wrinkled shape. The wrinkled shape may be useful for enhancing the adsorption of chemical vapors onto the surface of the foil due to the geometrical disruption of the smooth laminar flow of sample gas within the sample tube.

According further to the system described herein, the controller for the source of electricity may include a temperature sensing device coupled to the foil. The coupling may be in the form of direct contact, such as with a low mass thermocouple or RTD, or indirect contact, such as optical communication using an infrared temperature sensor. The low mass sensing device may be as low a mass as possible to avoid locally distorting the temperature of the cylindrically-shaped foil. The controller for the source of electricity may adjust the flow of electricity to maintain the foil at a prescribed temperature. One or more prescribed temperatures may be selected according to a predetermined sequence to permit at least one of the condensation of chemical vapor on the inside of the cylinder formed by the foil, the selective desorption of condensed chemical vapor from the inside of the cylinder formed by the foil based on the physical properties of a selected condensed chemical vapor species, the decomposition of condensed chemical vapor on the inside of the cylinder formed by the foil, and the transmission of chemical vapor through the cylinder formed by the foil.

According further to the system described herein, a method of rapidly heating and cooling a sample tube allows a selected range of chemical species to be transmitted as freely as possible through the sample tube. The sample tube may be heated to a specific temperature to facilitate the transmission of the sample gas. After the sample gas has been analyzed, the temperature of the sample tube may be rapidly changed, desirably increased, to desorb any condensed sample gas adhering to the inside surface of the sample tube. The temperature increase may also be sufficient to decompose at least some of the species contained within the sample gas.

According further to the system described herein, for the rapid purging of the sample tube, the temperature may be increased at a rapid rate (e.g., flash heated), desirably in excess of 25 degrees Celsius per second. This may be accomplished by both incorporating as little mass as possible in the thin foil as well as providing a source of electricity with sufficient Watts of output given the mass and heat capacity of the thin foil. The thin foil tube may also able to be decreased in temperature at a rate of at least 10 degrees Celsius per second. A foil with excessive mass will not be able to cool sufficiently rapidly to provide a conveniently short purging cycle and return to the normal transmission operating temperature. Thus, it is desirable for the foil to be as thin as possible without loss of structural integrity.

It is known to use an aluminum gas sample tube that is 1 cm inside diameter with 1 mm wall thickness. According to an embodiment of the system described herein, an 8 micron thick Kapton foil, wrapped into a 1 cm diameter tube would need to absorb 0.54% as many Joules of energy per unit length as the aluminum tube to reach the same temperature. Cooling speed is often a major limitation for rapid thermal cycling, since suitably high current power supplies can be provided to heat the aluminum tube as rapidly as possible. The thin Kapton foil heater, according to the system described herein, will cool as much as 185 times faster than the aluminum tube of the same inside diameter.

According further to the system described herein, the thin foil may be made of a polyimide, such as Kapton, that is coated with a metal, such as gold. The purpose of a gold coating is to avoid oxidation. Other low oxidation metals, such as indium, silver, copper, nickel, chromium, cobalt, aluminum, the noble metals, and some alloys containing substantially these elements, may be used. The conductive coating on the polyimide may include one or more metals, such as a first layer of nickel and a second layer of gold. Multiple coating layers may be employed to combine the higher electrical resistivity of one metal with the oxidation resistance of another. The conductive coating may also be in the form of conducting oxides, such as tin oxide and indium tin oxide.

The foil may further be first coated with at least one electrically insulating material to fully encapsulate the foil from the emission of undesirable vapor when heated. An embodiment may include a polyimide foil that is first coated with silica and then second coated with at least one metal. Other examples of an electrically insulating low vapor emission coating include, but are not limited to, ceramic oxides, such as SiON, alumina, zirconia, CaO, and yttria. The electrically insulating coating has the further advantage of presenting an inert inorganic substance if exposed to chemically reactive sample gas.

In another embodiment, the clamping mechanism may include an outer swaging ring or cylindrical ring that has at least one split along a radial line. This split allows the ends of the thin foil to pass radially outward through the ring. This geometry allows external access to the conductive surface on the inside of the thin foil. An external clamp, a spring, or other mechanism for squeezing the split ends of the outer swaging ring or cylindrical ring tightly closed may be provided in order to avoid gas leaks in the sample tube. One purpose of this geometry is to allow the foil to be rapidly heated on the outside of the cylinder formed by the thin foil and other voltages to be presented on the inside of the cylinder formed by the thin foil. This geometry may be useful in the design of a tube with a voltage gradient, such as would be found in an ion mobility spectrometer drift tube. The configuration would permit the drift tube to be rapidly thermally heated and subsequently cooled, which may be desirable for thermal decontamination of the tube from condensed sample gas impurities.

A configuration of tubing may be a tee-shaped junction of two tubes, possibly, but not necessarily, at right angles. This configuration may be created using foil cylindrical tubes by employing the outer swaging ring or cylindrical ring as one component of a clamp against the intersecting thin cylindrical tube. A second clamp ring may then be attached to squeeze the intersecting thin cylindrical tube in a gas tight seal.

Another configuration of tubing may be a blanked-off tube end. This configuration may be useful for closing the ends of a drift tube for an ion mobility spectrometer. It may also be useful for creating an angled joint between two tubes when a blanked-off tube end is combined with the tee-shaped junction of two tubes.

Another configuration of tubing may be a thin cylindrical tube with a mask containing an aperture within the tube. This configuration may be useful for pneumatically separating zones within a drift tube for an ion mobility spectrometer. It may also be useful for making the electric field more uniform within an ion mobility spectrometer and masking ions that are moving in an excessively radial direction. It may also be useful for mounting grids and electrical gates within an ion mobility spectrometer.

According further to the system described herein, a device for purging condensed chemical vapor from an inside surface of a gas sampling tube includes a foil with an electrically-conducting surface. A first clamping mechanism clamps the foil into an annular shape at a first end of the annular shape. A second clamping mechanism clamps the foil into the annular shape at a second end of the annular shape. A source of electricity provides a flow of electricity through the first clamping mechanism, the foil, and the second clamping mechanism in order to heat the foil. At least one separator separates the first clamping mechanism and the second clamping mechanism. A controller controls the source of electricity to heat the foil at a rate of at least 25 degrees Celsius per second, wherein the controller controls a temperature sequence including at least one temperature of the thin film according to performance of at least one of: condensing chemical vapor, transmitting chemical vapor, desorbing condensed chemical vapor, and decomposing condensed chemical vapor. The controller may include a temperature sensing device coupled to the foil. The source of electricity may be connected between the first and second clamp mechanisms. The separator may be electrically insulating and may be in the form of a plurality of rods, an annular tube, an annular tube with windows, and/or a connection to a remotely located rigid structure. At least one of the first and second clamping mechanisms may include at least one radial slot that permits the foil to be routed external to the first and second clamping mechanisms. The foil clamped in the annular shape may be joined to a second foil clamped in another annular shape in a tee-shaped pneumatic union, may be closed on at least one end by a foil blank off connection, and/or may have an internal structure including a mask with an aperture, the mask being disposed with a normal axis to a surface of the mask centered on an axis of the foil clamped in the annular shape. The foil may cool at a rate of at least 10 degrees Celsius per second. At least one of the first clamping mechanism and second clamping mechanism may be twisted about a common central axis of the clamping mechanisms to wrinkle a surface of the foil clamped in the annular shape, wherein a twist of the foil is maintained by fixed connections to the separator. The wrinkles in the foil surface may geometrically disrupt the smooth laminar flow of sample gas through the annular shape formed by the foil and assist in the concentration of chemical vapor.

According further to the system described herein, a device for purging condensed chemical vapor from a gas sampling tube includes a foil with an electrically-conducting surface, wherein the foil may provide for at least one of: heating of the foil at a rate of at least 25 degrees Celsius per second in response to a flow of electricity through the foil, and cooling of the foil a rate of at least 10 degrees Celsius per second after stopping the flow of electricity. At least one clamping mechanism may clamp the foil into an annular shape, wherein the at least one clamping mechanism is electrically coupled to the foil. A support provides structural rigidity to the annular shape. A controller may be included that controls the flow of electricity through the foil. The controller may control a temperature sequence including at least one a temperature of the foil according to performance of at least one of: condensing chemical vapor, transmitting chemical vapor, desorbing condensed chemical vapor, and decomposing condensed chemical vapor.

BRIEF DESCRIPTION OF THE DRAWINGS

Embodiments of the system described herein are explained with reference to the several figures of the drawing, discussed as follows.

FIGS. 2A and 2B are schematic diagrams illustrating fabrication of a rapidly heated and cooled tube that provides rapid purging of condensed chemical vapor from the inside surface of the tube according to an embodiment of the system described herein.

FIGS. 3C and 3D are schematic diagrams illustrating fabrication of a rapidly heated and cooled tube that provides rapid purging of condensed chemical vapor from the inside surface of the tube according to another embodiment of the system described herein.

FIG. 4 is a schematic diagram illustrating fabrication of a rapidly heated and cooled tube that provides rapid purging of condensed chemical vapor from the inside surface of the tube and further permits access to the electrically conducting components on the inside surface of the tube according to an embodiment of the system described herein.

FIG. 7 is a schematic diagram illustrating fabrication of a rapidly heated and cooled tube that provides rapid purging of condensed chemical vapor from the inside surface of the tube and further permits a thin foil mask with an aperture within the thin foil tube according to an embodiment of the system described herein.

FIG. 8 is a schematic diagram illustrating fabrication of a rapidly heated and cooled tube that provides rapid purging of condensed chemical vapor from the inside surface of the tube according to another embodiment of the system described herein.

DETAILED DESCRIPTION OF VARIOUS EMBODIMENTS

Figure 1:
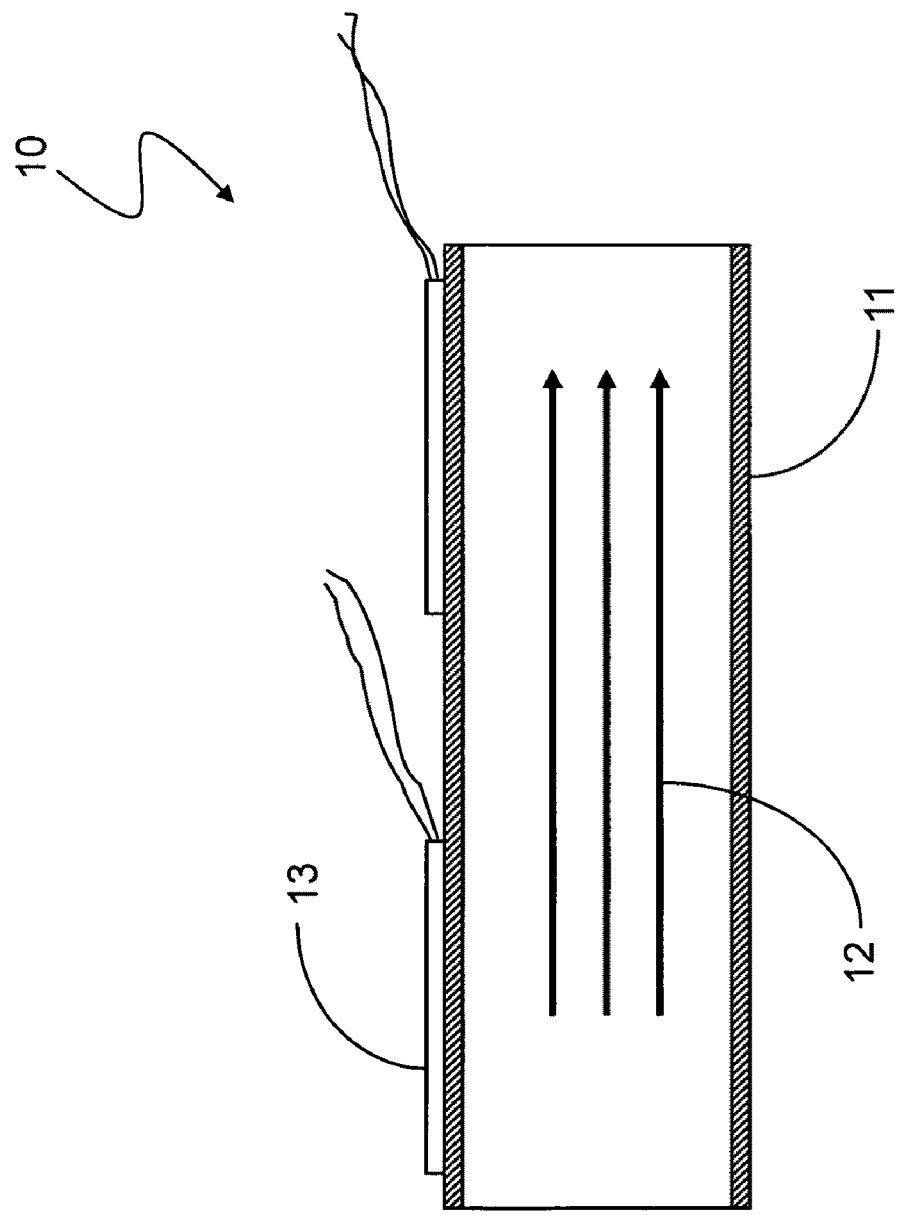
FIG. 1 is a diagram of a section of heated tubing known in the prior art.

Referring now to the figures of the drawing, the figures comprise a part of this specification and illustrate exemplary embodiments of the described system. It is to be understood that in some instances various aspects of the system may be shown schematically or may be exaggerated or altered to facilitate an understanding of the system.

In FIG. 1, a tube 10 according to the prior art is shown that includes a metal cylinder 11, an interior flow of chemical sample gas 12, and heating elements 13. The heating elements 13 may contain integrated temperature sensing devices, or a temperature sensing device may be provided in a separate package. The temperature sensing device may be an optical non-contact sensor and/or a sensor substantially in contact with the heated cylinder 11.

FIGS. 2A and 2B are schematic diagrams illustrating fabrication of a rapidly heated and cooled tube 100 that provides rapid purging of condensed chemical vapor from the inside surface of the tube according to an embodiment of the system described herein. FIG. 2A is a side cross-sectional view and FIG. 2B is an end view. The thin foil 110 is wrapped into a cylindrical shape using one or more clamping mechanisms 120. In an embodiment, the clamping mechanism 120 may include a cylindrical ring 111 and a cone-shaped swaging ring 112. Clamping mechanisms may be present at both ends of the cylinder and are held apart and structurally stiffened by one or more spacers and/or separators 114. Electrical connections 115 on each clamping mechanism 120 may be used to provide a flow of electricity through the conducting surface of the cylinder formed by the thin foil 110. Sample gas 102 flows through the inside of the cylinder formed by the thin foil 110. The electrical connection between the cylinder formed by the thin foil 110 and the one or more clamping mechanisms 120 may be assisted by an optional soft metal interface 113. In an embodiment, the soft metal interface 113 may be a small radius wire formed of a soft metal, such as gold, indium, silver, copper, nickel, tin, lead, and/or some alloys containing substantially these elements and/or exhibiting at least substantially the same characteristics.

In various embodiments, the clamp mechanism 120 may embed the foil between two swaging rings, between a cylindrical ring and a snap ring, and/or between a cylindrical ring and a circular spring as further discussed elsewhere herein. The clamp mechanism 120 may further optionally include at least one of a deformable electrically conductive metal o-ring, a deformable electrically conductive metal wire, and a deformable electrically conductive metal foil in contact with the electrically conducting surface of the foil in order to improve the transport of electricity between the clamp mechanism and the foil. Examples of deformable electrically conductive metal suitable for use with the system described herein include gold, indium, silver, copper, nickel, tin, lead, and/or some alloys containing substantially these elements and/or exhibiting at least substantially the same characteristics.

In another embodiment, the clamping mechanism 120 may include an outer swaging ring or cylindrical ring that has at least one split along a radial line. This split allows the ends of the thin foil 110 to pass radially outward through the ring. This geometry allows external access to the conductive surface on the inside of the thin foil. An external clamp, a spring, or other mechanism for squeezing the split ends of the outer swaging ring or cylindrical ring tightly closed may be provided in order to avoid gas leaks in the sample tube 100. One purpose of this geometry is to allow the thin foil to be rapidly heated on the outside of the cylinder formed by the thin foil 110 and other voltages to be presented on the inside of the cylinder formed by the thin foil 110. This geometry may be useful in the design of a tube with a voltage gradient, such as would be found in an ion mobility spectrometer drift tube. The configuration may permit the drift tube to be rapidly thermally heated and subsequently cooled, which may be desirable for thermal decontamination of the tube from condensed sample gas impurities.

Figures 3A, 3B:
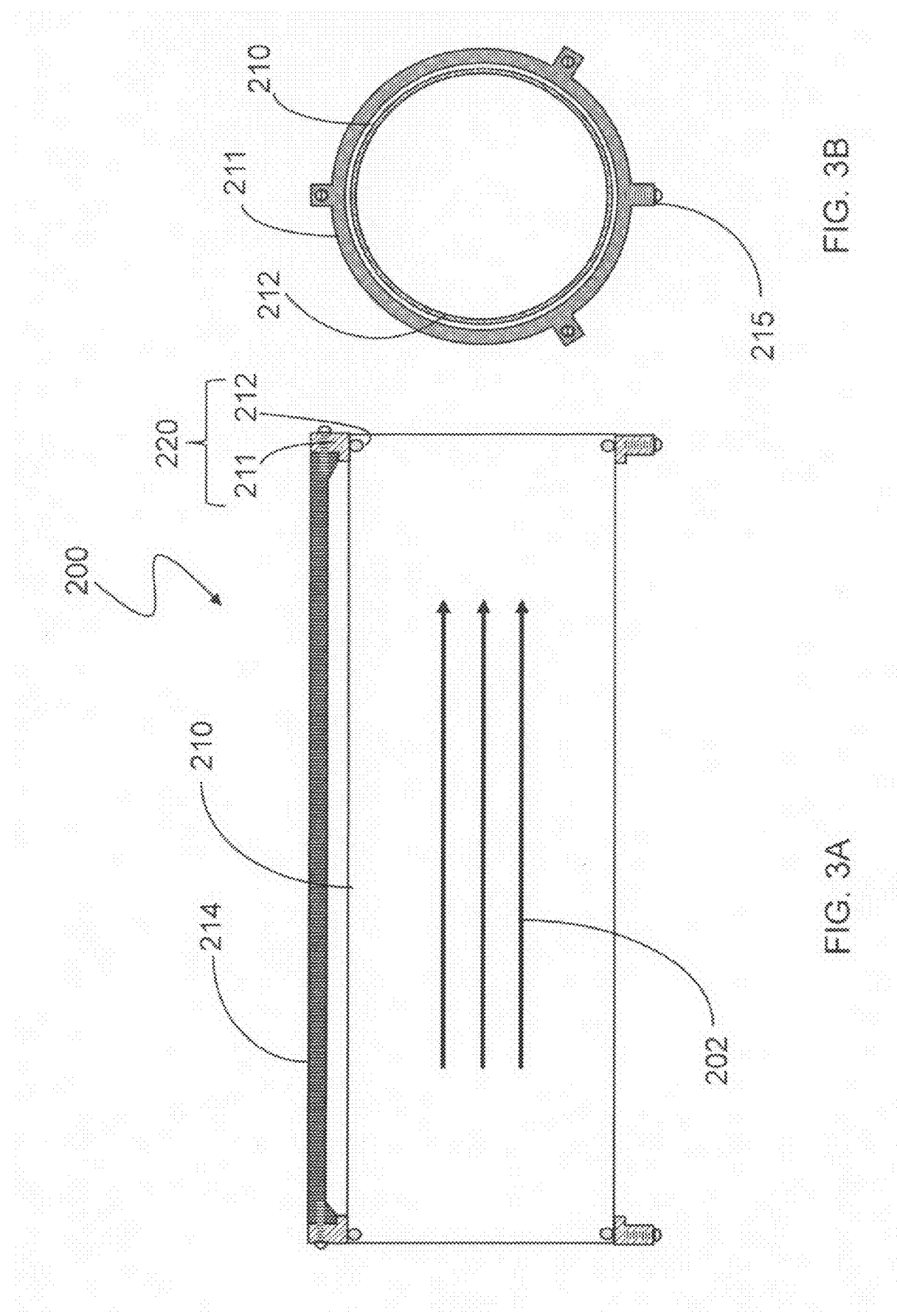
FIGS. 3A and 3B are schematic diagrams illustrating fabrication of a rapidly heated and cooled tube that provides rapid purging of condensed chemical vapor from the inside surface of the tube according to another embodiment of the system described herein.

FIGS. 3A and 3B are schematic diagrams illustrating fabrication of a rapidly heated and cooled tube 200 that provides rapid purging of condensed chemical vapor from the inside surface of the tube according to another embodiment of the system described herein. FIG. 3A is a side cross-sectional view and FIG. 3B is an end view. A thin foil 210 is wrapped into a cylindrical shape using one or more clamping mechanisms 220. In an embodiment, the clamping mechanism 220 may include a cylindrical ring 211 and a cylindrical spring and/or a snap ring 212. Clamping mechanisms may be present at both ends of the cylinder and may be held apart and structurally stiffened by spacers 214. Electrical connections 215 on each clamping mechanism 220 may be used to provide a flow of electricity through the conducting surface of cylindrically-shaped thin foil 210. Sample gas 202 flows through the inside of the cylinder formed by the thin foil 210.

FIGS. 3C and 3D are schematic diagrams illustrating fabrication of a rapidly heated and cooled tube 250 that provides rapid purging of condensed chemical vapor from the inside surface of the tube according to another embodiment of the system described herein. FIG. 3C is a side cross-sectional view and FIG. 3D is an end view. A thin foil 260 is wrapped into a cylindrical shape using one or more clamping mechanisms 270. In an embodiment, the clamping mechanism 270 may include a cylindrical ring 261 and a cylindrical spring and/or a snap ring 262. Clamping mechanisms may be present at both ends of the cylinder and may be held apart and structurally stiffened by electrically insulating annular cylindrical spacer 264. Electrical connections 265 on each clamping mechanism 270 may be used to provide a flow of electricity through the conducting surface of cylindrically-shaped thin foil 260. Sample gas 252 flows through the inside of the cylinder formed by the thin foil 260. In this embodiment, the clamping mechanisms 270 are twisted a few degrees relative to one another about the axis 271 of the cylindrical tube 250. Thin foil 260 is thereby wrinkled in a complex pattern that may disrupt the smooth laminar flow of sample gas 252 as it traverses the cylindrical tube 250. Annular cylindrical spacer 264 may be used to hold the twist and maintain the wrinkled shape. This geometry may be useful for enhancing the condensation of sample gas on the surface of cylinder formed by the thin foil 260 and may be used to fabricate a chemical concentrator, specifically the wrinkles may geometrically disrupt the smooth laminar flow of sample gas through the annular shape formed by the foil and assist in the concentration of chemical vapor.

FIG. 4 shows a schematic diagram of a tube 300 according to the system described herein in which the inside surface of a cylindrically-shaped thin foil 310 is accessible from outside of cylindrically-shaped thin foil 310 in order to make electrical connections to internal conducting surfaces. This geometry may be useful in the design of a drift tube for an ion mobility spectrometer, and the external electrical connections may be for the high voltage that defines an electric field within the drift tube. The thin foil 310 may be formed into a cylinder by a clamping mechanism, which may include a cylindrical ring 311 and a circular spring and/or snap ring 312. The thin foil 310 may be routed through a radial slot in the clamping mechanism, and the electrically conducting pattern on the inside surface of the cylinder formed by the thin foil 310 may be electrically connected to terminations on a circuit board 316. In an embodiment, the radial slot in the clamping mechanism may be squeezed into an air tight seal against the cylinder formed by the thin foil 310 by a screw 314 and a spring 315. In other embodiments, there may be two or more radial slots in the clamping mechanism in order to allow other electrical connections or provide orientation of a mask on the inside of the cylinder formed by the thin foil 310.

Figure 5:
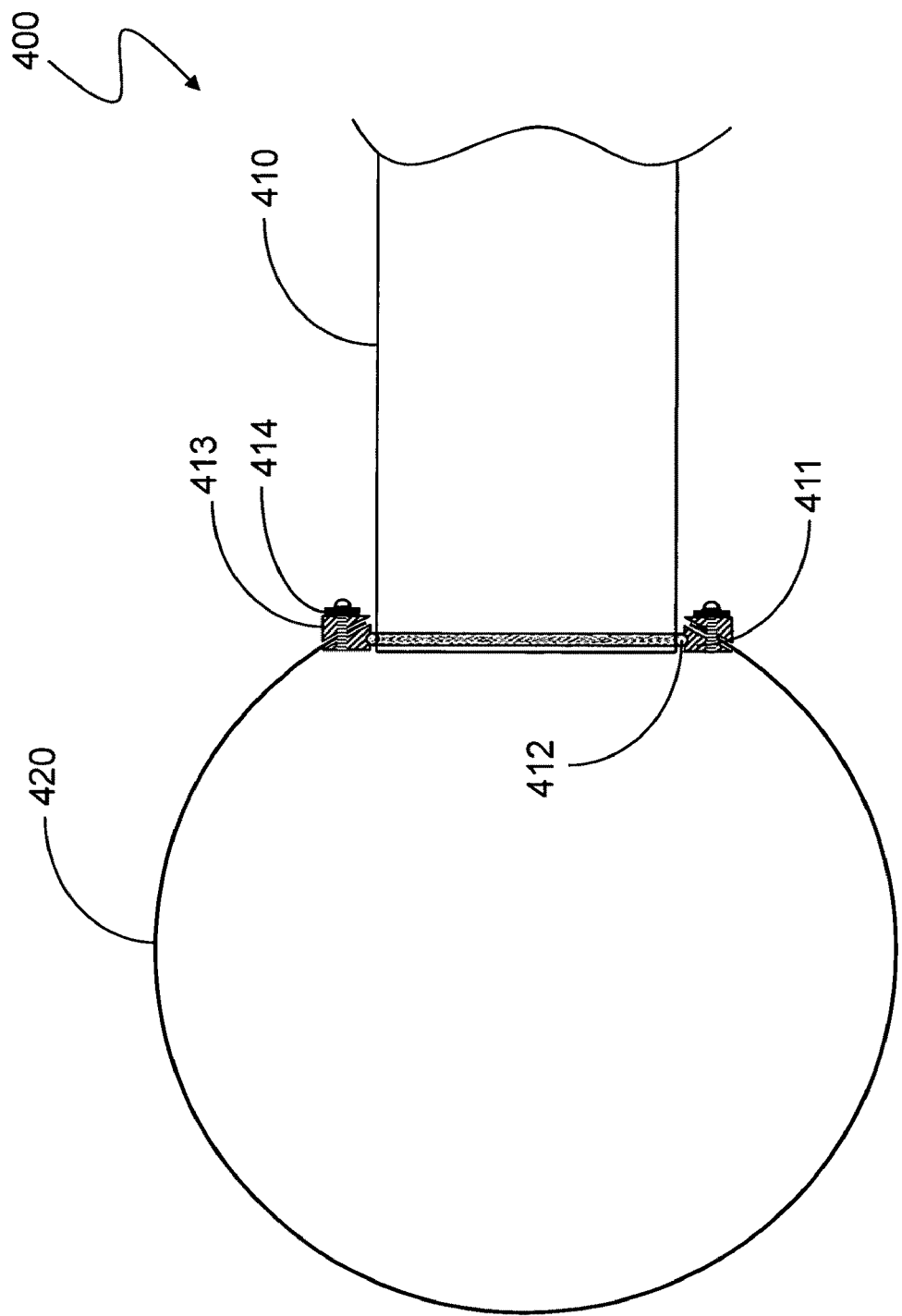
FIG. 5 is a schematic diagram illustrating fabrication of a rapidly heated and cooled tube that provides rapid purging of condensed chemical vapor from the inside surface of the cylindrical tube and further permits the tee-connection union of two such tubes according to an embodiment of the system described herein.

FIG. 5 is a schematic diagram of an embodiment 400 of the system described herein in which a cylindrical foil tube 410 is joined at an angle to another cylindrical foil tube 420 in order to make a tee joint. The tee-shaped junction of the two tubes may be at any desirable angle, including, for example, a right angle. A clamping mechanism at the end of the cylindrical foil tube 410 may include a shaped cylindrical ring 411 and a circular spring and/or a snap ring 412. The cylindrical foil tube 410 and its clamping mechanism may be inside and squeezed against the inside surface of the other cylindrical foil tube 420. An external clamp ring 413 may be employed to maintain the squeeze force and create a gas tight seal at the joint using a combination of screw and spring 414. The external clamp ring 413 may also provide an attachment point to complete the circuit for passing electricity through the cylindrical foil tube 410 and/or other cylindrical foil tube 420.

Figures 6A, 6B:
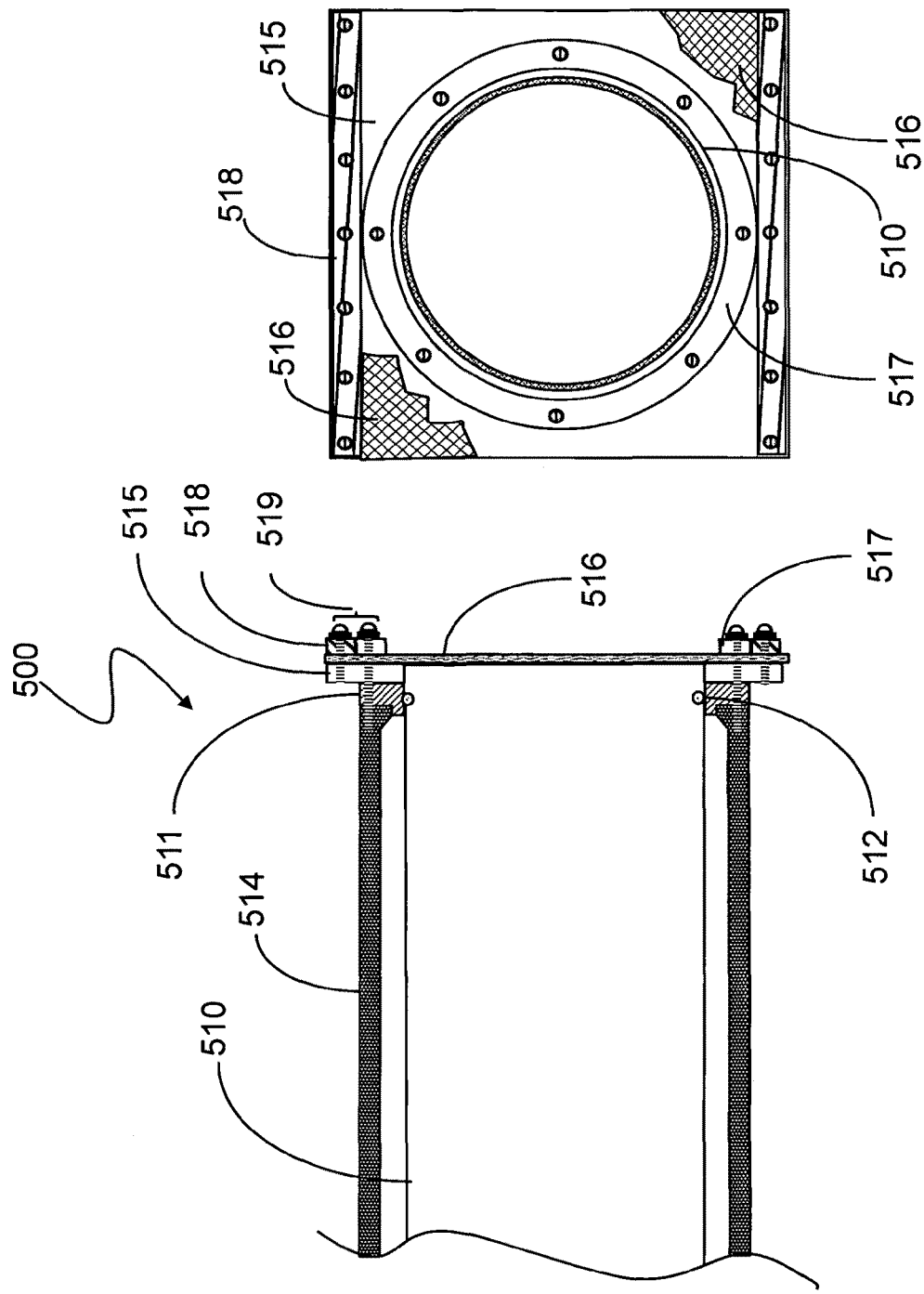
FIGS. 6A and 6B are schematic diagrams illustrating fabrication of a rapidly heated and cooled tube that provides rapid purging of condensed chemical vapor from the inside surface of the tube and further permits a thin foil blank-off of the end of the thin foil cylindrical tube according to an embodiment of the system described herein.

FIGS. 6A and 6B are schematic diagrams of an embodiment 500 of the system described herein in which a thin foil blank-off 516 is added to the end of the thin foil cylinder 510. FIG. 6A is a side cross-sectional view and FIG. 6B is an end view. If combined with the thin foil tee-connection illustrated in FIG. 5, an angled thin foil joint may also be provided. The thin foil 510 may be formed into a cylinder using a clamping mechanism provided by a cylindrical ring 511 and a circular spring and/or snap ring 512. One or more stiffeners 514 may be used to impart structural stability. A square or rectangular shaped electrically insulating end plate 515 may be squeezed against the cylindrical ring 511. The electrically insulating end plate 515 prevents electrical current that is passing through the thin foil blank-off 516 from interfering and shorting out electrical current that is passing through the thin foil 510. A clamping ring 517 may squeeze and seal the thin foil blank-off 516 using the combination of a screw and spring 519. A bus bar 518 evenly distributes electrical current across the thin foil blank off 516. The bus bar 518 may also be split into a plurality of shorter segments in order to avoid wrinkling of thin foil blank-off 516 due to thermal expansion mismatch. The above-noted embodiment may be useful for closing the ends of a drift tube for an ion mobility spectrometer. It may also be useful for creating an angled joint between two tubes when a blanked-off tube end is combined with the tee-shaped junction of two tubes further discussed elsewhere herein.

Figures 6C, 6D:
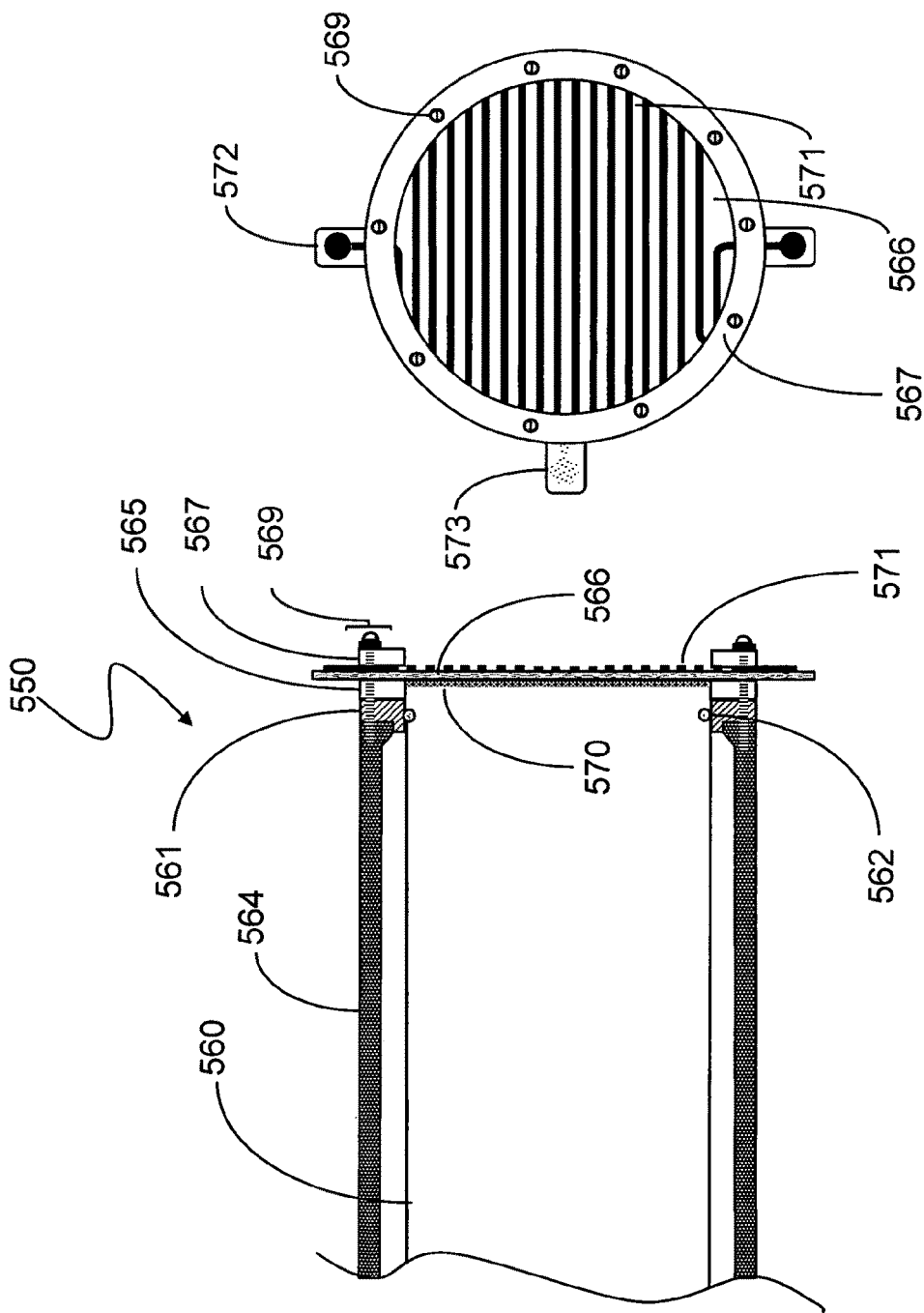
FIGS. 6C and 6D are schematic diagrams illustrating fabrication of a rapidly heated and cooled tube that provides rapid purging of condensed chemical vapor from the inside surface of the tube and further permits a thin foil blank-off of the end of the thin foil cylindrical tube according to another embodiment of the system described herein.

FIGS. 6C and 6D are schematic diagrams of another embodiment 550 of the system described herein in which a thin foil blank-off 566 is added to the end of the thin foil cylinder 560. FIG. 6C is a side cross-sectional view and FIG. 6D is an end view. If combined with the thin foil tee-connection illustrated in FIG. 5, an angled thin foil joint may also be provided. The thin foil 560 may be formed into a cylinder using a clamping mechanism provided by a cylindrical ring 561 and a circular spring and/or snap ring 562. One or more stiffeners 564 may be used to impart structural stability. An annular shaped electrically insulating end plate 565 may be squeezed against the cylindrical ring 561. The electrically insulating end plate 565 prevents electrical current that is passing through the thin foil blank-off 566 from interfering and shorting out electrical current that is passing through the thin foil 560. A clamping ring 567 may squeeze and seal the thin foil blank-off 566 using the combination of a screw and spring 569. An electrical tab connection 573 evenly distributes electrical voltage across the electrically conducting inside side 570 of thin foil blank off 566. The electrical tab connections 572 may join to a pattern 571 on the outside side of thin foil blank off 566 for providing heating. The above-noted embodiment may be useful for closing the ends of a drift tube for an ion mobility spectrometer. It may also be useful for creating an angled joint between two tubes when a blanked-off tube end is combined with the tee-shaped junction of two tubes further discussed elsewhere herein. It may further be useful for allowing one voltage to be displayed on the inside surface of thin foil blank off 566 and providing a separate heater that is electrically isolated from the inside surface of thin foil blank off 566.

FIG. 7 is a schematic diagram of a sample tube 600 according to an embodiment of the system described herein in which a thin foil mask 615 with an aperture is positioned within a cylinder formed by a thin foil 610. The thin foil 610 may be formed into the cylinder using a clamping mechanism provided by a cylindrical ring 611 and a circular spring and/or snap ring 612. In an embodiment, the clamping mechanism may have two split positions in order to more conveniently make electrical connections to the thin foil mask 615 using a plurality of circuit boards 616. The clamping mechanism may squeeze and seal the cylinder formed by the thin foil 610 using a combination of springs and screws 614. An optional electrically conductive pattern 617 for heating the thin foil mask 615 may be coated on the thin foil mask 615. In another embodiment, the conductive pattern 617 may be used to form an equi-potential surface on the thin foil mask 615. Optional stiffener rods 618 may be positioned parallel to the axis of the cylinder formed by the thin foil 610 in order to more accurately position the thin foil mask 615 than may be obtained solely by the extensions of the thin foil mask 615 that penetrate to the vicinity of the circuit boards 616. The thin foil mask 615 with an aperture may have extended tabs that penetrate out to the circuit boards 616. These tabs may be twisted to allow the thin foil mask 615 to be oriented with a normal axis with respect to a flat surface thereof substantially centered on the axis of the cylinder formed by the thin foil 610.

FIG. 8 is a schematic diagram illustrating a sample tube 700 that may be rapidly heated and cooled and that provides rapid purging of condensed chemical vapor from the inside surface of the tube according to another embodiment of the system described herein. A thin foil 710 may be wrapped into an annular shape using one or more clamping mechanisms. The thin foil 710 may be trapezoidal shaped so that the thin foil 710 is wrapped into a cone shape of variable diameter, as illustrated. As further described elsewhere herein, cylinders, cones and/or other annular shapes may be used in various embodiments for sample tubes of fixed cross sectional diameter and/or variable cross sectional diameter. Other shapes may also be appropriately used in connection with the system described herein. Orifices may be positioned at suitable locations in the thin foil 710 to permit tee-connections to other tubes. In an embodiment, a first clamping mechanism including a cylindrical ring 711*a* and a cylindrical spring and/or a snap ring 712*a* may be clamped at one end of the cone formed by the thin foil 710 and a second clamping mechanism including a cylindrical ring 711*b* and a cylindrical spring and/or a snap ring 712*b* may be positioned at the other end of the cone formed by the thin foil 710. The clamping mechanisms may be held apart and structurally stiffened by one or more separators 714. Electrical connections 715 on each clamping mechanism may be used to provide a flow of electricity through the conducting surface of the thin foil 710. Sample gas 702 flows through the inside of the cone-shaped thin foil 710.

In various embodiments suitable for the system described herein, the foil may be a thin foil, with characteristics as discussed herein, and made of a metal foil, a polymer coated with a conducting material, a flexible ceramic coated with a conducting material, and/or a laminate of metal and electrical insulator. The metal foil may be selected from: an alloy containing nickel, such as Inconel, a low thermal expansion alloy, such as Invar, and a stainless steel. The metal foil may be a composite of two or more metals. The polymer that is coated with a conducting material may have a melting or decomposition point greater 200 degrees Celsius. The polymer that is coated with a conducting material may be selected from a polyimide, such as Kapton, an aramid, such as Nomex, a fluorocarbon, such as Teflon, and/or a polyether ketone, such as polyetheretherketone (PEEK). The flexible ceramic may be a form of mica.

In other embodiments, the thin foil may be made of polyimide, such as Kapton, that is coated with a metal, such as gold. The purpose of a gold coating is to avoid oxidation. Other low oxidation metals, such as indium, silver, copper, nickel, chromium, cobalt, aluminum, the noble metals, and some alloys containing substantially these elements, may be used. The conductive coating on the polyimide may include or more metals, such as a first layer of nickel and a second layer of gold. Multiple coating layers may be employed to combine the higher electrical resistivity of one metal with the oxidation resistance of another. The conductive coating may also be in the form of conducting oxides, such as tin oxide and indium tin oxide.

The thin foil may further be first coated with at least one electrically insulating material to fully encapsulate the foil from the emission of undesirable vapor when heated. An embodiment may include a polyimide foil that is first coated with silica and then second coated with at least one metal. Other examples of an electrically insulating low vapor emission coating include, but are not limited to, ceramic oxides, such as SiON, alumina, zirconia, CaO, and yttria. The electrically insulating coating has the further advantage of presenting an inert inorganic substance if exposed to chemically reactive sample gas.

In another embodiment, a core of the thin foil may be an electrical insulator. An electrically conducting coating or laminate, as further discussed elsewhere herein, may be uniformly distributed on at least one face of the thin foil, distributed in a pattern on at least one face of the thin foil, or in any combination thereof. A uniform distribution may be inexpensive to prepare and useful for heating the thin foil uniformly. A patterned distribution may be useful for special applications, such as creating a thermal gradient or forming a voltage gradient. A combination of a uniform distribution on one face and a patterned distribution on the other may be useful for combining uniform heating and the formation of a voltage gradient. The same combination in another embodiment may be useful for combining a uniform voltage and substantially uniform heating.

Figure 9:
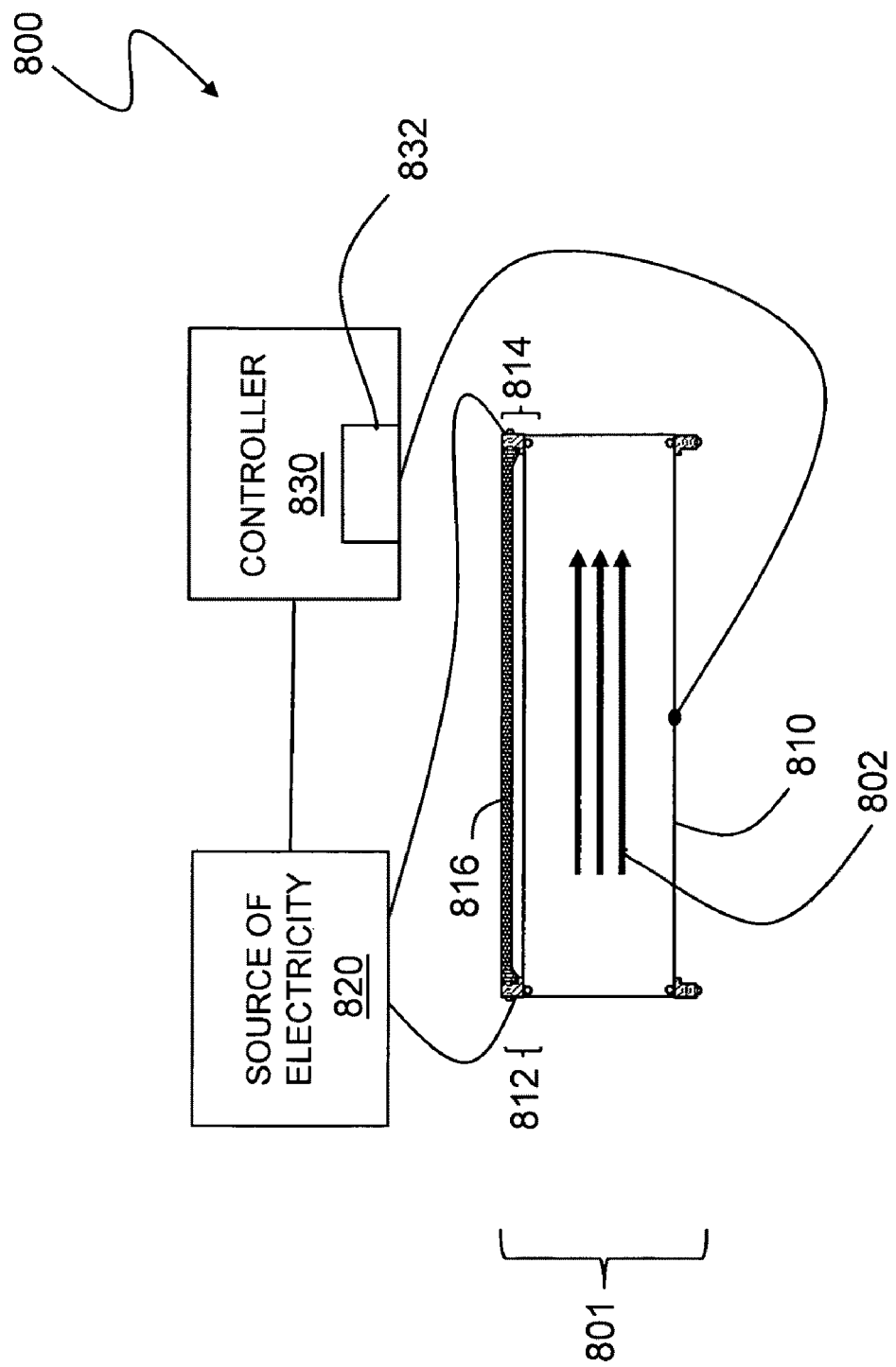
FIG. 9 is a schematic diagram showing a sample tube coupled to a source of electricity and a controller according to an embodiment of the system described herein.

FIG. 9 is a schematic diagram 800 showing a sample tube 801 coupled to a source of electricity 820 and a controller 830 according to an embodiment of the system described herein. The sample tube 801 may represent any of the various embodiments illustrated herein and/or different embodiment(s) and may include a foil 810 shaped into an annular shape, such as a cylinder, using a first clamping mechanism 812 and a second clamping mechanism 814 which are separated by a structural separator 816. The source of electricity 820 and the controller 830 may be used in connection with the characteristics of the foil 810, and other components of the sample tube 801, as discussed elsewhere herein, to rapidly heat and cool the sample tube 801 in accordance with the system described herein and allows a selected range of chemical species in a sample gas 802 to be transmitted as freely as possible through the sample tube 801. The sample tube 801 may be heated to a specific temperature in accordance with the controller 830 controlling the flow of electricity from the source of electricity 820 to the sample tube 801 to facilitate the transmission of the sample gas 802. After the sample gas 802 has been analyzed, the temperature of the sample tube 801 may be rapidly changed by control of the controller 830, desirably increased, to desorb any condensed sample gas adhering to the inside surface of the cylinder formed by the foil 810. The temperature increase may also be sufficient to decompose at least some of the species contained within the sample gas. In an embodiment, for the rapid purging of the sample tube 801, the temperature may be increased at a rapid rate (e.g., flash heated), desirably in excess of 25 degrees Celsius per second. This may be accomplished by both incorporating as little mass as possible in the thin foil as well as providing a source of electricity with sufficient Watts of output given the mass and heat capacity of the thin foil 810 and controlling the flow of electricity accordingly. Flash heating in a short time period may desorb any condensed or adsorbed chemicals in a highly concentrated burst, thus enhancing the detection capability of a downstream chemical detector. Flash heating may also purge the sample tube of contamination in a short time period. The thin foil 810 may also be able to be decreased in temperature at a rate of at least 10 degrees Celsius per second, for example, when the flow of electricity is stopped. A foil with excessive mass may not be able to cool sufficiently rapidly to provide a conveniently short purging cycle and return to the normal transmission operating temperature. Thus, it is preferable for the thin foil to be as thin as possible without loss of structural integrity.

For example, the use of aluminum gas sample tubes are known that having a 1 cm inside diameter with 1 mm wall thickness. According to an embodiment of the system described herein, a foil 810 made of an 8 micron thick Kapton foil, wrapped into a 1 cm diameter cylinder, would need to absorb 0.54% as many Joules of energy per unit length as the aluminum tube to reach the same temperature. Cooling speed is often a major limitation for rapid thermal cycling, since suitably high current power supplies can be provided to heat the aluminum tube as rapidly as possible. The thin Kapton foil, according to the system described herein, will cool as much as 185 times faster than the aluminum tube of the same inside diameter.

In an embodiment, the source of electricity 820 may be connected between the first and second clamp mechanisms 812, 814. The structural separator 816 of the first and second clamp mechanisms 812, 814 may be electrically insulating and may be in the form of hollow tubing, rod spacers, and/or a connection to an external rigid frame. The separator 816 may further include thermal insulation.

As shown in FIG. 9, the controller 830 for the source of electricity 820 may include a temperature sensing device 832 coupled to the thin foil 810. The coupling may be in the form of direct contact, such as with a low mass thermocouple or RTD, or indirect contact, such as optical communication using an infrared temperature sensor. The low mass sensing device may be as low a mass as possible to avoid locally distorting the temperature of the thin foil 810. The controller 830 for the source of electricity 820 may adjust the flow of electricity to maintain the thin foil 810 at a prescribed temperature. One or more prescribed temperatures may be selected according to a predetermined sequence to permit at least one of the condensation of chemical vapor on the inside of the cylinder formed by the thin foil 810, the selective desorption of condensed chemical vapor from the inside of the cylinder based on the physical properties of a selected condensed chemical vapor species, the decomposition of condensed chemical vapor on the inside of the cylinder, and the transmission of chemical vapor through the cylinder. Note, that in various embodiments, the sample tube 801, the source of electricity 820 and the controller 830 may be integrated in a single physical unit and/or may be separate components.

The system described herein for rapidly heating and cooling a tube and providing of purging of condensed chemical vapor from the inside surface of the tube described herein may be in combinations of the embodiments described herein and may incorporate other features, alone or in any combination, including without limitation features described in commonly assigned U.S. patents: U.S. Pat. Nos. 6,828,795, 6,861, 646, and 6,888,128; U.S published patent applications 2005-0007119 A1, 2003-0155504 A1, 2004-0248319 A1, and 2004-0227073 A1; and U.S. provisional applications 60/357, 394, 60/357,618, 60/363,485, and 60/473,649, all of which are incorporated herein by reference.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method according for providing a gas sampling tube, comprising:
   providing a foil with an electrically-conducting surface;
   clamping, with a first clamping mechanism, the foil into an annular shape at a first end of the annular shape;
   clamping, with a second clamping mechanism, the foil into the annular shape at an opposite second end of the annular shape;
   supplying a flow of electricity sequentially through the first clamping mechanism, the foil, and the second clamping mechanism in order to heat the foil;
   separating the first clamping mechanism and the second clamping mechanism to provide structural rigidity to the annular shape; and
   controlling the flow of electricity to heat the foil at a rate of at least 25 degrees Celsius per second, wherein a temperature sequence including at least one temperature of the foil is controlled according to performance of at least one of: condensing chemical vapor, transmitting the chemical vapor, desorbing condensed chemical vapor, and decomposing condensed chemical vapor, and wherein the foil is one of: a metal, a polymer with an electrically conductive coating, a flexible ceramic with an electrically conductive coating, a laminate of an electrically conductive material and an electrically insulating material.

2. The method according to claim 1, wherein the metal is selected from a group consisting of: an alloy containing nickel, a low thermal expansion alloy, and a stainless steel.

3. The method according to claim 1, wherein at least one of the polymer and the flexible ceramic has a melting or decomposition temperature greater than 200 degrees Celsius.

4. The method according to claim 3, wherein the polymer is selected from the group consisting of: a polyimide, an aramid, a fluorocarbon, and a polyether ketone, and wherein said flexible ceramic is a form of mica.

5. The method according to claim 1, wherein at least one of the electrically conductive coating and the electrically conductive material is selected from the group consisting of: gold, indium, silver, copper, nickel, chromium, cobalt, aluminum, the noble metals, alloys containing substantially these elements, and electrically conductive oxides.

6. The method according to claim 1, wherein the foil is first coated with an electrically insulating material prior to the addition of at least one of the electrically conductive coating and said electrically conductive material.

7. A method for providing a gas sampling tube, comprising:
   providing a foil with an electrically-conducting surface;
   clamping, with a first clamping mechanism, the foil into an annular shape at a first end of the annular shape;
   clamping, with a second clamping mechanism, the foil into the annular shape at an opposite second end of the annular shape;
   supplying a flow of electricity sequentially through the first clamping mechanism, the foil, and the second clamping mechanism in order to heat the foil;
   separating the first clamping mechanism and the second clamping mechanism to provide structural rigidity to the annular shape; and
   controlling the flow of electricity to heat the foil at a rate of at least 25 degrees Celsius per second, wherein a temperature sequence including at least one temperature of the foil is controlled according to performance of at least one of: condensing chemical vapor, transmitting the chemical vapor, desorbing condensed chemical vapor, and decomposing condensed chemical vapor, and wherein at least one of the first clamping mechanism and the second clamping mechanism includes at least one of: two swaging rings; a cylindrical ring and a snap ring; a cylindrical ring and a circular spring; a deformable electrically conductive metal o-ring; a deformable electrically conductive metal wire; and a deformable electrically conductive metal foil in contact with the electrically conducting surface of the foil in order to improve the conduction of electricity at an interface of the foil and the o-ring.

8. The method according to claim 7, wherein the deformable electrically conductive metal is formed from at least one of: gold, indium, silver, copper, nickel, tin, lead, and alloys containing substantially these elements.

9. A method for providing a gas sampling tube, comprising:
providing a foil with an electrically-conducting surface;
clamping, with a first clamping mechanism, the foil into an annular shape at a first end of the annular shape;
clamping, with a second clamping mechanism, the foil into the annular shape at an opposite second end of the annular shape;
supplying a flow of electricity sequentially through the first clamping mechanism, the foil, and the second clamping mechanism in order to heat the foil;
separating the first clamping mechanism and the second clamping mechanism to provide structural rigidity to the annular shape;
controlling the flow of electricity to heat the foil at a rate of at least 25 degrees Celsius per second, wherein a temperature sequence including at least one temperature of the foil is controlled according to performance of at least one of: condensing chemical vapor, transmitting the chemical vapor, desorbing condensed chemical vapor, and decomposing condensed chemical vapor; and
twisting at least one of the first clamping mechanism and the second clamping mechanism about a common central axis of the clamping mechanisms to wrinkle a surface of the foil clamped in the annular shape, wherein a twist of the foil is maintained by fixed connections to the separator.

10. A method for providing a gas sampling tube, comprising:
providing a foil with an electrically-conducting surface:,
clamping, with a first clamping mechanism, the foil into an annular shape at a first end of the annular shape;
clamping, with a second clamping mechanism, the foil into the annular shape at an opposite second end of the annular shape;
supplying a flow of electricity sequentially through the first clamping mechanism, the foil, and the second clamping mechanism in order to heat the foil;
separating the first clamping mechanism and the second clamping mechanism to provide structural rigidity to the annular shape;
controlling the flow of electricity to heat the foil at a rate of at least 25 degrees Celsius per second, wherein a temperature sequence including at least one temperature of the foil is controlled according to performance of at least one of: condensing chemical vapor, transmitting the chemical vapor, desorbing condensed chemical vapor, and decomposing condensed chemical vapor, and wherein the temperature of the foil is controlled to permit at least one of: (i) condensation of chemical vapor on the inside surface of the gas sampling tube, (ii) selective desorption of condensed chemical vapor from the inside surface of the gas sampling tube based on the physical properties of a selected condensed chemical vapor species, (iii) decomposition of condensed chemical vapor on the inside surface of the gas sampling tube, and (iv) transmission of chemical vapor through the gas sampling tube.

11. A device for purging condensed chemical vapor from a gas sampling tube, comprising:
a foil with an electrically-conducting surface;
a first clamping mechanism that clamps the foil into an annular shape at a first end of the annular shape;
a second clamping mechanism that clamps the foil into the annular shape at a second end of the annular shape;
a source of electricity that provides a flow of electricity through the first clamping mechanism, the foil, and the second clamping mechanism in order to heat the foil;
at least one separator that separates the first clamping mechanism and the second clamping mechanism and provides structural rigidity to the annular shape; and
a controller that controls the source of electricity to heat the foil at a rate of at least 25 degrees Celsius per second, wherein the controller controls a temperature sequence including at least one temperature of the foil according to performance of at least one of: condensing chemical vapor, transmitting chemical vapor, desorbing condensed chemical vapor, and decomposing condensed chemical vapor, and wherein at least one of the following is provided: (i) the separator is electrically insulating; (ii) the controller includes a temperature sensing device coupled to the foil, (iii) said source of electricity is connected between the first and second clamp mechanisms, (iv) at least one of the first and second clamping mechanisms includes at least one radial slot that permits the foil to be routed external to the first and second clamping mechanisms, (v) the foil clamped in the annular shape is joined to a second foil clamped in another annular shape in a tee-shaped pneumatic union, (vi) the foil clamped in the annular shape has an internal structure including a mask with an aperture, the mask being disposed with a normal axis to a surface of the mask centered on an axis of the foil clamped in the annular shape, and (vii) at least one of the first clamping mechanism and the second clamping mechanism is twisted about a common central axis of the clamping mechanisms to wrinkle a surface of the foil clamped in the annular shape, wherein a twist of the foil is maintained by fixed connections to the separator.

12. A device for purging condensed chemical vapor from a gas sampling tube, comprising:
a foil with an electrically-conducting surface;
a first clamping mechanism that clamps the foil into an annular shape at a first end of the annular shape;
a second clamping mechanism that clamps the foil into the annular shape at a second end of the annular shape;
a source of electricity that provides a flow of electricity through the first clamping mechanism, the foil, and the second clamping mechanism in order to heat the foil;
at least one separator that separates the first clamping mechanism and the second clamping mechanism and provides structural rigidity to the annular shape;
a controller that controls the source of electricity to heat the foil at a rate of at least 25 degrees Celsius per second, wherein the controller controls a temperature sequence including at least one temperature of the foil according to performance of at least one of: condensing chemical vapor, transmitting chemical vapor, desorbing condensed chemical vapor, and decomposing condensed chemical vapor; and a thin foil blank off connection that closes the foil clamped in the annular shape on at least one end.

13. The device according to claim 12, further comprising:
a heater disposed on an outer surface of the thin foil blank off that is electrically isolated from an inside surface of the thin foil blank off.

14. A device for purging condensed chemical vapor from a gas sampling tube, comprising:
a foil with an electrically-conducting surface;
a first clamping mechanism that clamps the foil into an annular shape at a first end of the annular shape;
a second clamping mechanism that clamps the foil into the annular shape at a second end of the annular shape;
a source of electricity that provides a flow of electricity through the first clamping mechanism, the foil, and the second clamping mechanism in order to heat the foil;
at least one separator that separates the first clamping mechanism and the second clamping mechanism and provides structural rigidity to the annular shape; and
a controller that controls the source of electricity to heat the foil at a rate of at least 25 degrees Celsius per second, wherein the controller controls a temperature sequence including at least one temperature of the foil according to performance of at least one of: condensing chemical vapor, transmitting chemical vapor, desorbing condensed chemical vapor, and decomposing condensed chemical vapor, and wherein the foil cools at a rate of at least 10 degrees Celsius per second.

15. A device for purging condensed chemical vapor from a gas sampling tube, comprising:
a foil with an electrically-conducting surface, wherein the foil provides for at least one of: heating of the foil at a rate of at least 25 degrees Celsius per second in response to a flow of electricity through the foil, and cooling of the foil a rate of at least 10 degrees Celsius per second after stopping the flow of electricity;
at least one clamping mechanism that clamps the foil into an annular shape, wherein the at least one clamping mechanism is electrically coupled to the foil;
a support that provides structural rigidity to the annular shape; and
a controller that controls the flow of electricity through the foil.

16. The device according to claim 15, wherein the controller controls a temperature sequence including at least one temperature of the foil according to performance of at least one of: condensing chemical vapor, transmitting chemical vapor, desorbing condensed chemical vapor, and decomposing condensed chemical vapor.

* * * * *